(12) United States Patent
Jo

(10) Patent No.: US 10,213,278 B2
(45) Date of Patent: Feb. 26, 2019

(54) METHOD AND TOOLS FOR INDIRECT BRACKET POSITIONING

(71) Applicant: Yong-Min Jo, Duesseldorf (DE)

(72) Inventor: Yong-Min Jo, Duesseldorf (DE)

( * ) Notice: Subject to any disclaimer, the term of this patent is extended or adjusted under 35 U.S.C. 154(b) by 0 days.

(21) Appl. No.: 15/885,285

(22) Filed: Jan. 31, 2018

(65) Prior Publication Data

US 2018/0153652 A1 Jun. 7, 2018

Related U.S. Application Data

(62) Division of application No. 14/758,423, filed as application No. PCT/EP2013/078166 on Dec. 31, 2013, now Pat. No. 9,925,020.

(30) Foreign Application Priority Data

Dec. 31, 2013 (GB) .................................. 1223522.2

(51) Int. Cl.
*A61C 7/14* (2006.01)
*A61C 13/34* (2006.01)

(52) U.S. Cl.
CPC .............. *A61C 7/146* (2013.01); *A61C 13/34* (2013.01)

(58) Field of Classification Search
CPC ................................ A61C 7/146; A61C 13/34
USPC ............................................................ 433/3
See application file for complete search history.

(56) References Cited

U.S. PATENT DOCUMENTS

| 5,971,754 A | 10/1999 | Sondhi et al. |
| 2005/0233276 A1 | 10/2005 | Kopelman et al. |
| 2006/0172247 A1 | 8/2006 | Abels et al. |
| 2010/0279243 A1* | 11/2010 | Cinader, Jr. ........... A61C 7/146 433/3 |

OTHER PUBLICATIONS

International Search Report and Written Opinion for International Application No. PCT/EP2013/078166 dated Apr. 24, 2014, 10 pages.
Doerfer, Stefan, "Untersuchung der Uebertragungsgenauigkeit verschiedener Methoden des indirekten Klebens—Dissertation," Department of Medicine—Charite—University Medicine Berlin; Retrieved from the Internet: http://www.diss.fu-berlin.de/diss/receive/FUDISS_thesis_000000002797?lang=en. Feb. 19, 2010.

* cited by examiner

*Primary Examiner* — Paula J Stice
(74) *Attorney, Agent, or Firm* — Abel Law Group, LLP

(57) ABSTRACT

The invention provides an improved method of indirect positioning of orthodontic brackets wherein a positive tooth model is utilized which comprises a model tooth, a mock bracket and a place holder for the mock bracket. The positive tooth model can be used for making a transfer tray for accommodating and transferring a bracket onto a tooth of a patient, wherein said transfer tray comprises a form-fitting cavity for the distal portion of the bracket. Further provided are transfer trays and positive tooth models for use in said method.

6 Claims, 3 Drawing Sheets

US 10,213,278 B2

METHOD AND TOOLS FOR INDIRECT BRACKET POSITIONING

CROSS-REFERENCE TO RELATED APPLICATION(S)

The present application is a divisional of U.S. patent application Ser. No. 14/758,423, filed Jun. 29, 2015, entitled "Method and Tools For Indirect Bracket Positioning" naming Inventor Yong-Min Jo, which is a 371 National Stage of International Application No. PCT/EP2013/078166, filed December 2013, entitled "Method and Tools For Indirect Bracket Positioning" naming Inventor Yong-Min Jo, which claims the benefit under 35 U.S.C. 119(e) of GB Application No. 1223522.2, filed Dec. 31, 2012, entitled "Method and Tools For Indirect Bracket Positioning" naming Inventor Yong-Min Jo which are all incorporated by reference herein in their entireties.

BACKGROUD OF THE INVENTION

1. Field of the Invention

The present invention concerns the field of orthodontics. More specifically, the present invention relates to a method and tools for positioning brackets on teeth of a patient.

2. Discussion of Background Information

In orthodontics one aim for moving teeth of a patient into appropriate positions such that the teeth can fulfill their function optimally, and such that an aesthetically pleasing appearance of the teeth is achieved. For moving teeth within a patient's mouth, an orthodontist may use so-called aligners which essentially represent negative models of the patient's teeth. Alternatively a set of braces or orthodontic brackets may be used, wherein a bracket is positioned on and attached to each tooth of a patient, and a rectangular metal arc wire is mounted into the slot openings of the brackets for engaging the forces rendering the teeth to move into the desired positions.

The orthodontic brackets may be positioned directly on the teeth within the patient's mouth. As the form and position of each bracket determines the movement of the tooth said bracket is attached to, it is apparent that an accurate positioning of each of the brackets on the patient's teeth is important for achieving the desired movements. However, accurate direct positioning of brackets on the teeth of a patient inside the patient's mouth is a difficult task.

For improving accuracy of directly positioning brackets on the teeth it is known to utilize jigs. For example U.S. 2007/0031775 A1 teaches a placement jig for locating an orthodontic appliance on a tooth. The placement jig is provided with a cavity formed in the jig body and conforming the contour of an occlusal portion of a tooth crown, which cavity is coated with a releasable adhesive to hold the jig to the tooth as the orthodontic appliance is bonded to the tooth. A connecting structure is fixed to the jig body, and appliance receiving structures are machined on each jig body during the jig's manufacturing.

For further improving the accuracy of bracket positioning, "indirect" methods have been developed, wherein the brackets are positioned on a three-dimensional positive tooth model of the patient's teeth outside the patient's mouth rather than directly on a tooth within the patient's mouth. Positioning the brackets on a positive tooth model improves visualization and permits using measuring devices for more precisely determining the position of the brackets. When the brackets are positioned on and releasably bonded to the teeth of the positive tooth model, a transfer tray is fabricated and used for transferring the brackets from the positive tooth model to the patient's mouth. U.S. Pat. Nos. 4,952,142 and 5,971,754 disclose variations of indirect positioning methods.

However, there are drawbacks in these conventional bracket positioning systems and methods. Typical brackets comprise a broad flat base for attaching the bracket to the tooth, and structures protruding from the base thereby forming a rectangular slot for receiving an arc wire. Typical brackets also comprise structures called "tie-wings" which are used to anchor a disposable ligature. Because of the necessity of these structural elements, the brackets must possess a certain degree of structural profile height and shape irregularity. The structural profile and shape irregularity render it difficult to remove the transfer tray from the patient's teeth once the brackets have been transferred from the positive tooth model and bonded to the patient's teeth, in particular because the transfer tray is form-fitting the brackets for securely holding the brackets in place during their transfer to the patient's mouth.

Hence, there is a desire for improving the method of indirect positioning of brackets, and it is an object of the present invention to provide an improved method for indirect positioning of brackets.

The object is achieved by a method of indirect positioning brackets utilizing a positive tooth model, using said positive tooth model for manufacturing a transfer tray for accommodating at least one bracket, and using said transfer tray for positioning and adhering the at least one bracket onto the patient's tooth or teeth.

SUMMARY OF THE INVENTION

Figure 1A:
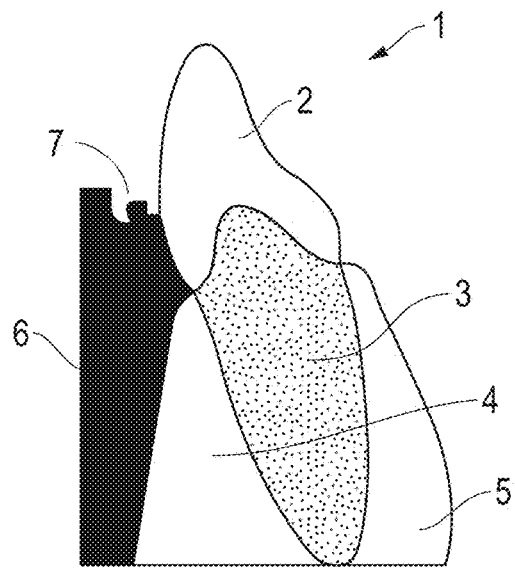
FIG. 1A displays a schematic representation of a cross-section from a positive tooth model of the lower jaw trough an incisor.

In a first aspect, the invention provides a method for positioning and adhering at least one bracket onto a tooth of a patient, wherein a positive tooth model is provided and/or a transfer tray for accommodating and transferring at least one bracket onto a tooth of a patient, wherein said transfer tray comprises at least one cavity for accommodating the distal part of the bracket in a form-fitting manner, and wherein said transfer tray is formed by utilizing said positive tooth model.

In a second aspect, the invention provides a transfer tray for positioning and attaching at least one bracket to a tooth of a patient, wherein said transfer tray comprises at least one cavity for accommodating the at least one bracket, said at least one cavity being configured to accommodate the distal part of the at least one bracket in form-fitting manner.

In a third aspect, the invention provides a positive tooth model comprising at least one place holder or apron, said at least one place holder or apron extending along the vertical axis of a model tooth perpendicular at least from the horizontal median of the position for placing a bracket onto said tooth to the portion of the positive tooth model representing the gum.

DETAILED DESCRIPTION OF THE INVENTION

The present invention will be described with respect to particular embodiments, but the invention is not limited thereto, but only to the claims. Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under, beyond and the like in the description and in the claims are used for descriptive purposes and not necessarily for describing relative positions. It is to be understood that the terms so used are interchangeable under appropriate circumstances and that the embodiments of the invention described herein are capable of operation in other orientations than described or illustrated herein. It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

According to the first aspect, the invention provides a method for positioning and adhering at least one bracket onto a tooth of a patient, wherein a positive tooth model is utilized and/or a transfer tray for accommodating and transferring at least one onto a tooth of a patient, wherein said transfer tray comprises at least one form-fitting cavity for the distal portion of the bracket.

In an embodiment of the first aspect, a method for positioning and adhering at least one bracket onto a tooth of a patient, wherein a positive tooth model is provided which comprises at least one mock bracket and/or a transfer tray for accommodating and transferring at least one bracket onto a tooth of a patient, wherein said transfer tray comprises at least one cavity for accommodating the distal part of the bracket in a form-fitting manner, and wherein said transfer tray is formed by utilizing said positive tooth model.

The method comprises the steps of providing a positive tooth model comprising at least one mock bracket, the at least one mock bracket comprises a fully formed distal part of a bracket, and a place holder instead of the proximal part of a bracket, the place holder extending perpendicular from the horizontal median of the at least one mock bracket to the portion of the positive tooth model representing the gum;

using said positive tooth model for preparing a transfer tray, said transfer tray comprises at least one cavity for accommodating a bracket, said at least one cavity being configured to accommodate the distal part of the bracket in form-fitting manner;

fitting a bracket into the at least one cavity of the transfer tray;

placing the transfer tray accommodating the at least one bracket onto the teeth of the patient within the patient's mouth;

filling the space between the at least one bracket and the tooth with a curable resin;

curing the curable resin thereby binding the at least one bracket to the tooth; and removing the transfer tray from the patient's mouth.

A typical orthodontic bracket comprises a base for attaching the bracket to the tooth, a rectangular slot for receiving an arc wire, and two tie wings, a proximal tie wing and a distal tie wing, wherein said two tie wings are separated from each other by the rectangular slot. The proximal tie wing is to be understood to be the tie wing being oriented towards the gum, whereas the distal tie wing of a bracket is the tie wing oriented towards the tooth crown when the bracket is bonded to the tooth.

The term "mock bracket" refers to a model of a bracket. Said model comprises the distal part of a bracket, i.e. fully formed distal tie wing(s), and optionally the rectangular slot. The mock bracket does not necessarily comprise the proximal part of a bracket in fully formed manner. Instead, it comprises a place holder instead of the proximal tie wings. The mock bracket may be made of any suitable material such as a metal or plastics. In addition, the term "mock brackets" comprises composition wherein a real bracket has been used, and wherein the proximal part of the bracket is covered with material such that the place holder is formed.

In an embodiment, the positive tooth model comprises a plurality of mock brackets, wherein only the distal part of each mock bracket in fully designed, whereas the proximal part of each mock bracket is designed as a filled place holder.

In another embodiment of the first aspect, a method is provided wherein the positive tooth model comprises at least one place holder or apron, but no mock bracket. Instead, the at least one place holder or apron is configured such that the proximal portion of a real bracket can be engaged into the distal end of the place holder or apron in a form-fitting manner.

The method according to the latter embodiment comprises the steps of providing a positive tooth model comprising at least one a place holder, the place holder extending perpendicular from the horizontal median of the position for placing a bracket at one tooth to the portion of the positive tooth model representing the gum, wherein the distal portion of said place holder or apron is formed as a negative model of the proximal portion of a bracket;

placing a bracket with its proximal portion into the distal portion of the at least one place holder or apron in a form-fitting manner;

using said positive tooth model including at least one bracket for preparing a transfer tray, said transfer tray comprises at least one cavity for accommodating a bracket, said at least one cavity being configured to accommodate the distal part of the bracket in form-fitting manner;

fitting a bracket into the at least one cavity of the transfer tray;

placing the transfer tray accommodating the at least one bracket onto the teeth of the patient within the patient's mouth;

filling the space between the at least one bracket and the tooth with a curable resin;

curing the curable resin thereby binding the at least one bracket to the tooth; and removing the transfer tray from the patient's mouth.

It may be advantageous to fit the bracket into the distal portion of a place holder or apron by means of a gripper.

In an embodiment, the place holder of at least one mock bracket, preferably of each mock bracket of the plurality of mock brackets, or the apron(s) is/are configured as tiny rod or protrusion extending in perpendicular direction, i.e. in essentially vertical direction from the horizontal median of the mock bracket or the position for placing a bracket onto the tooth to the portion of the positive tooth model representing the gum.

In an additional and/or alternative embodiment, at least one place holder is configured as a filled area covering the proximal parts of at least two neighboring mock brackets, wherein said filled area extends in essentially vertical direction from the horizontal median of the mock brackets to the portion of the positive tooth model representing the gum.

In a further and/or additional embodiment, the embodiment, the place holder or apron is wider than the bracket that should be fitted into its distal portion. In this configuration, the bracket is kept in place by the gripping force, and conventional sugar bonding of the bracket onto the model tooth appears unnecessary. The smaller the width of the place holder or apron, the better the gripping force of the tray to be formed by utilizing the positive tooth model provided with the at least one bracket. However, in the absence of sugar-bonding the bracket to the tooth, the bracket may get out of its place upon forming the transfer tray. Thus, in a preferred configuration, the place holder or apron has the same width as the bracket.

In an embodiment, the positive tooth model is manufactured by means of conventional modeling. That is, a cast of the patient's upper or lower jaw is made, and a positive tooth model generated in that the cast is filled with a suitable material, for example plaster. The resulting positive tooth model is designated "progenitor tooth model" in the sense of the invention, because it does not comprise a mock bracket, i.e. elements representing at least one bracket. The progenitor tooth model is then provided with at least one mock bracket, preferably with a plurality of mock brackets, which is/are positioned on and attached to the model teeth of the progenitor tooth model. Subsequently, a place holder for each of the mock brackets present on the progenitor tooth model is molded in form of a tiny rod or protrusion which extends perpendicular from the horizontal median of the corresponding mock bracket towards the portion of the tooth model representing the gum closest to the same tooth, and thereby replacing the proximal part of the corresponding bracket. In an additional or alternative embodiment, a place holder is molded which covers the proximal parts of at least two neighboring mock brackets.

In another embodiment, the progenitor tooth model is manufactured by means of rapid prototyping.

In an embodiment of the rapid prototyping of positive tooth models, a process is utilized wherein the model is built from site-directed photocuring of a resin. In this method, a solid three dimensional object is manufactured in that a projector projects so-called volumetric pixel (voxel) with dimensions as small as 16 μm×16 μm×15 μm in X, Y and Z direction into a liquid resin, which then cause the resin to cure from liquid to solid at this particular position within the liquid. Dynamic voxel thickness gives control over Z build thicknesses and the projector optics gives control over X and Y resolution.

In another embodiment, the rapid prototyping comprises an inkjet head 3D printing process for preparing the progenitor positive tooth model.

In a further embodiment, the method comprising an inkjet head 3D printing process for preparing the progenitor positive tooth model is a powder bed inkjet head 3D printing. In the powder bed inkjet head 3D printing process, an inkjet-like printing head moves across a bed of powder, selectively depositing a liquid binding material, i.e. binder, in the shape of the section or slice of the positive tooth model. A fresh layer of powder is spread across the top of the model, and the process of selectively depositing binder is repeated. When the tooth model is complete, unbound powder is removed.

In an embodiment of the powder bed inkjet head 3D printing process, software virtually cuts a virtual positive tooth model into digital cross sections, creating a two dimensional image for each layer. Each layer has a thickness of about 0.1 mm. A bed of powder is accurately and evenly spread across a build platform by using a feed piston and a platform which can be lowered incrementally for each layer. A roller mechanism spreads the powder fed from the feed piston onto the build platform such that an even, smooth and full layer of densely packed powder per layer results. Once the layer of powder is spread, the inkjet print head(s) print the cross sectional area of the cross section to be printed onto the layer of powder, binding the powder together. This process is repeated for all layers of the positive tooth model to be manufactured. Application of the binder to a given layer binds said layer to the previous layer too.

The powder for the inkjet head 3D powder bed printing is based on plaster and contains numerous additives that maximize surface finish, feature resolution, and part strength. Suitable powders are disclosed in WO 1998/009798 A1, and are commercially available from 3DSYSTEMS, Rock Hill, S.C., USA.

In an embodiment of the powder bed inkjet head 3D printing process, the thickness of each powder layer is about 0.09 to about 0.1 mm (0.0035 to 0.0004 inches). In another and/or alternative the binder is applied to each powder layer at a resolution of about 600 dpi (dots per inch). The spatial resolution resulting from the layer thickness and the density of binder dots applied to each powder layer permits manufacturing a positive tooth model that is smooth and accurate enough to be used in molding orthodontic appliances such that neither the positive tooth model nor the orthodontic appliance molded by said positive tooth model in a pressure molding or vacuum molding process requires extensive finishing to render the orthodontic appliance tightly and comfortably fitting the patient's teeth.

In an embodiment of the powder bed inkjet head 3D printing, the printed progenitor positive tooth model is infiltrated with a curable resin. The progenitor tooth model as obtained from the 3D powder bed inkjet head printing process is friable and would crumble in the course of vacuum molding. To provide a rigid positive tooth model that withstands vacuum molding, the progenitor tooth model is infiltrated with curable resin, preferably with a photocurable resin, and subsequently curing of the resin is effected, preferably by irradiating the progenitor tooth model with UV light. An example of a curable resin is selected from the group consisting of polyacralytes and polymethacrylates.

In an alternative embodiment of the inkjet head 3D printing process for preparing the progenitor positive tooth model, a process is used for manufacturing the positive tooth models, wherein layers of at least one photopolymer, i.e. a photopolymerizable polymer, are applied to the preceding layer and immediately cured after being applied.

In the printing process according to the alternative embodiment of the first aspect of the invention, an inkjet head moves back and forth along an x-axis, and applies a thin layer of photopolymerizable polymer on the platform or on the previous layer. Each layer of photopolymerizable polymer is cured before the next layer of photopolymerizable polymer is applied by means of ink jet head printing. Preferably, the photopolymerizable polymer is cured by exposing the layer of photopolymerizable polymer to UV-light. In a preferred embodiment of the ink jet head 3D printer, the ink jet head comprises a UV-lamp. Subsequent curing of the printed positive tooth model is not required.

In a further embodiment of the 3D ink jet head printing processes, colored tooth models are manufactured, wherein colored lines indicate the positions for each bracket on each model tooth and/or indicates the line along which the transfer tray should be excised from a vacuum molded or pressure molded polymer film. In the powder bed inkjet head 3D printing process, colored binders are used for 3D printing. In a further embodiment, binders of different color are applied to the powder bed by means of a single inkjet head. Usually, the printing head has channels for different colored binders, typically four different colored binders are used: cyan, magenta, yellow and black. In an alternative embodiment, a plurality of inkjet heads are used, wherein one inkjet head is used for each of the differently colored binders such that a first inkjet head is used for applying a first binder having a first color, a second inkjet head is used for applying a second binder having a second color, a third inkjet head is used for applying a third binder having a third color, and another inkjet head is used for applying a binder having a fourth color. In using colored binders for 3D printing, multicolored positive tooth models can be manufactured.

In an embodiment the progenitor positive tooth model comprises at least one line and/or at least one area of different color than the main body of the progenitor positive tooth model. Preferably the progenitor tooth model comprises a plurality of lines and/or a plurality of areas having different color that the main body of the progenitor tooth model. Preferably, said line(s) and/or area(s) is/are present on a tooth or the tooth of the progenitor tooth model.

In a further embodiment, said at least one line or plurality of lines and/or the at least one area and/or plurality of areas are indicators for the position(s) of the brackets or mock brackets on the model teeth. Each colored area indicates the position of the bracket on the tooth, and horizontal lines indicate the direction of the horizontal median of the bracket, whereas vertical lines indicate the direction of the vertical median of the bracket when said bracket is positioned on the tooth with its base.

In an additional and/or alternative embodiment, the progenitor positive tooth model comprises at least one line having a different color than the main body of the progenitor positive tooth model, said line indicating the line along which a tray of thermoplastic polymer film should be excised from the molded thermoplastic polymer film.

In an additional and/or alternative embodiment, the progenitor positive tooth model comprises an elevated area on at least one of the model teeth, preferably on each of the model teeth compared to the original teeth, wherein said elevated area(s) represent(s) the adhesive to be used for attaching the brackets to the teeth, and wherein said elevated areas are indicative for the position of the brackets on the teeth. In an embodiment, at least one of said elevated areas represents a normal base for the bracket to be attached to said tooth. This embodiment is of particular advantage, because the elevated area compensates an individual curvature of the tooth, and standardizes brackets can be employed which do not have to be adapted to the surface contour of the tooth they are supposed to be adhered to. In another and/or alternative embodiment, at least one of said elevated areas represents a unique individual base for the bracket to be attached to the tooth. Unique individual base for brackets are used in methods comprising backward planning and generating a set-up. That is, a positive tooth model of the desired configuration of teeth at the end of the treatment is generated and used for configuring individual brackets for each of the teeth, each individual bracket comprising a unique base accounting for the peculiarities (curvature, position, movement to perform) of the corresponding tooth.

In a further embodiment, at least one of the elevated areas comprises an embossed rim. Preferably ails elevated areas comprise an embossed rim. The embossed rim provides guidance for positioning the bracket on the tooth, provided that the area within the embossed rim corresponds to the area of the bracket's base.

In a further embodiment, the elevated area and/or the embossed rim are of different color than the main body of the progenitor positive tooth model. The elevated area(s) and/or the embossed rim may have a different color than the colored line(s) present on the positive tooth model.

In a further embodiment, mock brackets are positioned on and attached to the progenitor tooth model made by means of rapid prototyping, preferably the brackets are positioned where indicated by means of colored and/or elevated areas, and/or indicated by colored lines on the model tooth. Then a place holder for each of the mock brackets present on the progenitor tooth model are molded in form of tiny rods or protrusions extending perpendicularly from the horizontal median of each mock bracket towards the portion of the tooth model representing the gum closest to the same tooth, and thereby replacing the proximal part of each mock bracket.

In another embodiment of the manufacturing of the positive tooth model, said positive tooth model is manufactured by means of rapid prototyping, and includes at least one partial mock bracket and the place holder for the proximal part of the mock bracket. Therefore, a digital model of the patient's upper and/or lower jaw is generated, either by direct scanning of the teeth within the patient's mouth or by scanning a model of the patient's teeth. By digital processing, virtual brackets are positioned on the virtual teeth, and the proximal portion of at least one virtual bracket is virtually molded to become a place holder virtually extending perpendicularly from the horizontal median of the virtual bracket towards the portion of the virtual tooth model representing the gum closest to the same virtual tooth in form of tiny rods or protrusions. The digital processing also permits virtually generating a place holder in form of a filled area covering the proximal parts of at least two neighboring mock brackets.

The data of the virtual positive tooth model including the at least one partial bracket is used for manufacturing a true positive tooth model by means of rapid prototyping as described herein above.

Digitally modeling the positive tooth model including brackets or at least partial brackets permits building up individualized brackets.

Individualized brackets or individual brackets are understood as brackets having a unique base. Said unique base for each bracket is obtained by a preceding set-up, wherein the positions of the teeth to be achieved is considered, and the bracket for each tooth is provided with a unique base mediating the movement of the tooth in the desired directions, i.e. a lateral movement in forward, backwards or sideward direction, and a turning movement around at least one of the X-, Y- and Z-axis of the tooth.

It is to be understood that the set-up may be made digitally or manually. In a manual set-up model teeth are cut from a positive tooth model of the patient or the teeth are manufactured individually, and then their position is rearranged such that a positive tooth model is obtained which represents the desired result.

In another embodiment, the manual set up is made in that the model teeth of the patient are manufactured individually, for example by modeling or by means of any known 3D printing process. The individually manufactured model teeth are mounted on a model gum of the patient's gum in an arrangement representing the desired positions of the teeth. In an embodiment, the individually manufactured model teeth are repositioned into the original position of the teeth by placing them into a mold of the original position and reconstructing the gum with a flexible material. The term "original position" refers to the status at diagnosing and prior to the treating of the patient. From this situation, the teeth can be manually moved into the desired position.

In an additional embodiment, the individually manufactured teeth being made by a 3D printing process are provided with at least one vertical and/or horizontal line having a different color than the model tooth. In an additional and/or alternative embodiment, the individually manufactured teeth being made by a 3D printing process are provided with at least one colored and/or elevated area. Said at least one line, colored area and/or elevated area provide a guidance or are helpful in rearranging the teeth in the desired position within the model gum.

The positive tooth model thus includes the model of the patient's jaw, at least one partial bracket positioned on one to the teeth, said partial bracket optionally comprising a unique base, and the place holder replacing the proximal part of the at least one bracket.

Figure 1B:
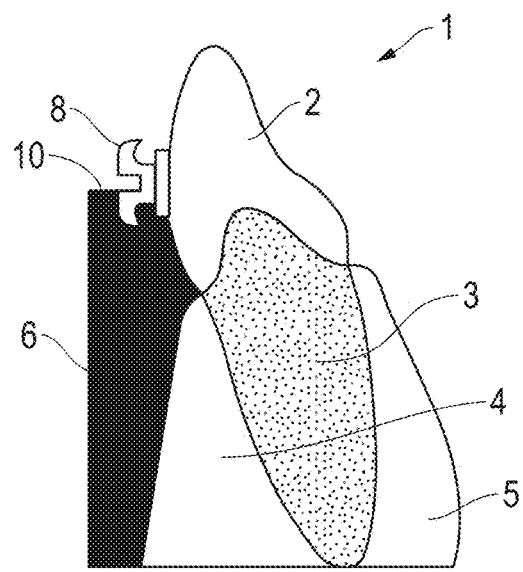
FIG. 1B displays the same cross-section as shown in FIG. 1A, including a bracket.
Figure 1C:
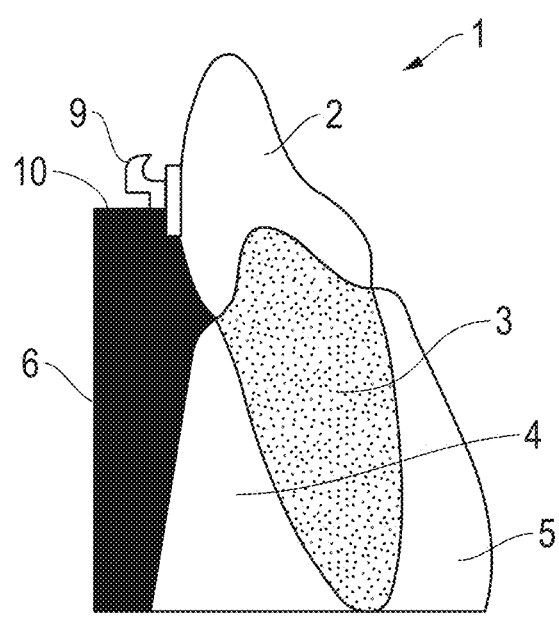
FIG. 1C displays a schematic representation of a cross-section from a positive tooth model of the lower jaw through an incisor including a mock-bracket according to one embodiment.

In an embodiment, as shown in FIG. 1C, the positive tooth model 1 comprises at least one mock bracket 9 comprising a fully formed distal part of a bracket, and a place holder 6 replacing the proximal part of the at least one mock bracket, the place holder 6 extending perpendicular from the horizontal median 10 of the at least one mock bracket to the portion of the positive tooth model representing the gum 4, along the longitudinal median of the corresponding model tooth.

In a further and/or alternative embodiment, the positive tooth model comprises at least one place holder or apron extending perpendicular from the horizontal median of the position at the model tooth where the bracket should be placed to the portion of the positive tooth model representing the gum, along the longitudinal median of the corresponding model tooth. The distal portion of said at least one place holder or apron is formed as a negative model of the bracket's proximal portion such that the proximal portion of the bracket fit into the distal portion of the place holder. This embodiment is illustrated in FIGS. 1A and 1B showing a cross sectional view of a positive tooth model 1 through an incisor of the lower jaw. The crown 2 and the root 3 of the model incisor are shown as well as the portions representing the outer gum 4 and the inner gum 5. Also shown is a place holder or apron 6 which is an integral part of the positive tooth model 1. As is shown in FIG. 1A, the apron 6 comprises a distal portion 7 which is configured as negative model of the proximal portion of a bracket 8.

Figure 2A:
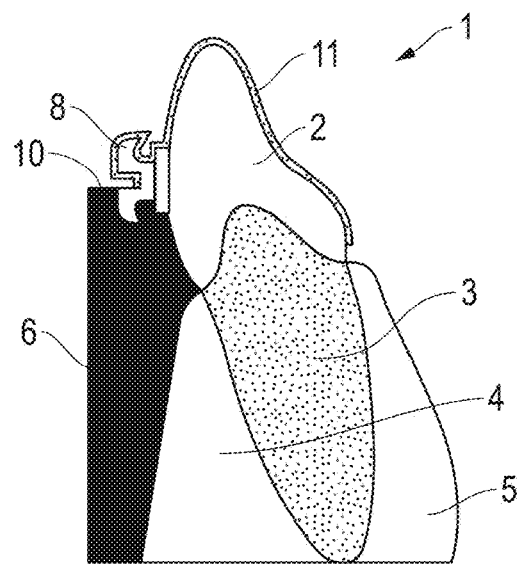
FIG. 2A displays the same cross-section from a positive tooth model as shown in FIG. 1B, further including a formed transfer tray using the tooth model.

The positive tooth model according to any one of the preceding embodiments provides a model for manufacturing a transfer tray 11 (see FIGS. 2A and 2B) by means of vacuum molding or pressure molding.

In an embodiment, a transfer tray for positioning and adhering at brackets onto the teeth of a patient is used, wherein the transfer tray comprises at least one cavity for accommodating a bracket. The at least one cavity is configured to accommodate the distal part of a bracket in a form-fitting manner. In another embodiment, the transfer tray comprises a plurality of cavities, wherein each cavity is configured to accommodate the distal part of a bracket in a form-fitting manner.

The transfer tray may be manufactured by any known methods. In an embodiment, the transfer tray is manufactured by casting a curable polymer composition over the positive tooth model. In an alternative embodiment, silicone may be pressed onto the positive tooth model in form of a bar or rod such that a negative form of the teeth of the positive tooth model is obtained which can optionally be further proceeds for obtaining the transfer tray.

In another embodiment, individual trays for each tooth may be manufactured by utilizing each of the model teeth of the positive tooth model comprising a mock bracket, and the resulting set of individual tray or jigs are assembled for providing a transfer tray.

Figure 2B:
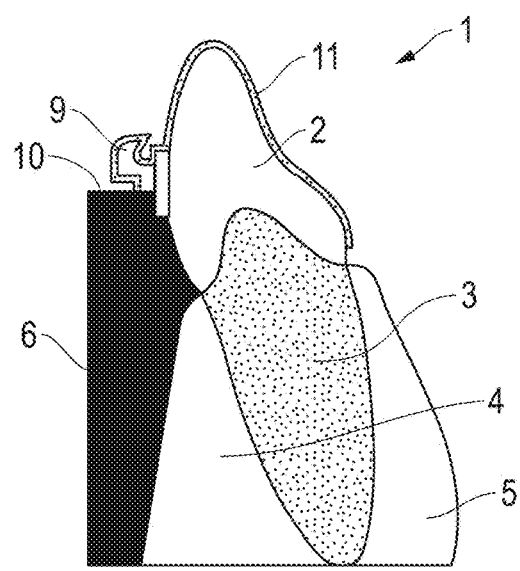
FIG. 2B displays the same cross-section from a positive tooth model as shown in FIG. 1C, further including a transfer tray using the tooth model.

In another embodiment, the transfer tray 11 is manufactured by means of vacuum molding or pressure molding utilizing the positive tooth model comprising the at least one mock bracket 9 (see FIG. 2B).

The transfer tray is preferably formed from a sheet of a suitable thermoplastic polymer film. The term "thermoplastic" refers to thermosoftening plastics, i. e. polymers that become pliable or moldable above a specific temperature, and return to a solid state upon cooling. Examples of suitable thermoplastic polymer films for forming transfer trays are available under the trade names BIOCRYL® "C", 1.5, 2, or 3 mm thick sheets of PMMA, BIOCRYL® "M", or DURAN®+, 0.5, 0.625, 0.75, 1.0, 1.5, or 2.0 mm thick sheets, from SCHEU-DENTAL GmbH, 58642 Iserlohn, Germany.

In manufacturing a transfer tray the transfer tray is formed from a sheet of the suitable thermoplastic polymer film by using a conventional pressure molding machine or vacuum molding machine. The molding machine forms a transfer tray directly from the positive tooth model and the desired thermoplastic polymer film. After molding, the solidified polymeric sheet is removed from the molding machine in conjunction with the positive tooth model. The positive tooth model is removed from the mold including the orthodontic appliance. The molded sheet of thermoplastic polymer comprises the shape of at least a part of the positive tooth model. The excess thermoplastic polymer material is removed so that only the transfer tray is obtained.

In another embodiment, the transfer tray is manufactured by means of vacuum molding in that a thin thermoplastic polymer sheet, preferably having a thickness of about 0.1 mm, is used as place holder film and subjected to a first vacuum molding step. Subsequently, the transfer tray is manufactured in that the sheet of thermoplastic polymer film is applied onto the molded place holder film and subjected to vacuum molding in a second vacuum molding step. Thereafter, the place holder film and molded thermoplastic polymer film are separated from each other, either before, during or after the transfer tray has been excised from the molded polymer film.

The transfer tray is excised from the molded thermoplastic polymer film or laminate along a line connecting the rectangular slots of the mock brackets. Typically, the positive tooth model remains present while the transfer tray is excised. The place holder(s) for the proximal part of the bracket(s) being included in the positive tooth model prevents any material of the thermoplastic polymer film from passing behind model structured, there by allowing removal of the molded thermoplastic film or the transfer tray from the positive tooth model without tearing off a mock bracket. Said mock bracket torn off the positive tooth model would clog a cavity within the transfer tray, and thus impair insertion of the real brackets to be positioned.

In still another embodiment, the transfer tray is manufactured by mean of rapid prototyping, i.e. the transfer tray is produced by three dimensional printing, such as those methods described herein above for manufacturing a positive tooth model. Thus, a digital model of the transfer tray is generated, based on digital data representing the patient's upper and/or lower jaw. Said digital data may be obtained by scanning the patient's teeth within the patient's mouth or by scanning a positive or negative model of the patient's teeth. Based on the digital data representing the patient's teeth or jaw, a set of data representing the digital model of the transfer tray is generated, and based on these data, the transfer tray is printed.

Manufacturing the transfer tray by a 3D printing method is beneficial in that the transfer tray does not need extensive finishing. Since the printing of the transfer tray can be started and/or ended at any virtual plane of the model, it is not necessary to excise the transfer tray from any excess polymer material.

The transfer tray represents a negative model of the patient's upper or lower jaw, wherein said transfer tray comprises cavities for accommodating brackets. The cavities are configured to accommodate the distal part of each bracket in a form-fitting manner. The cavities are configured such that they do not accommodate the proximal part of a bracket, because that portion of the cavity has been formed by the place holder rod or protrusion of the positive tooth model.

The brackets to the positioned onto the patient's teeth are fitted into the cavities within the transfer tray. Then the transfer tray is applied to the patient's jaw or teeth.

In an embodiment, the transfer tray is configured such that the base of each bracket is positioned within a distance from the tooth said bracket is to be attached to. Said distance represents the space wherein the resin and/of individual base of the bracket is present after the method has been completed. The space between each bracket and the corresponding tooth is then filled with a curable resin, preferably with a resin that is curable by being exposed to ultra violet light. Subsequently the resin is cured, for example in that the UV-curable resin is exposed to UV-light. After the resin has been cured, the transfer tray is removed from the patient's mouth, wherein the brackets remain attached to their teeth in the desired position. Any excess resin may be removed from the teeth, and the brackets are engaged in that an arc wire is mounted.

In another embodiment of the method, the transfer tray including the bracket(s) fitted into the at least one cavity, is placed onto a positive tooth model of the patient's teeth, preferably onto a plaster model of the patient's teeth. Then the space between each bracket and the corresponding plaster tooth is filled with a curable resin, preferably with a resin that is curable by being exposed to ultra violet light. Subsequently the resin is cured, for example in that the UV-curable resin is exposed to UV-light. After the resin has been cured, the transfer tray is removed from the plaster model of the patient's teeth and transferred to the patient's mouth where the transfer tray is placed on the teeth of the patient. A curable adhesive resin is introduced into the gap between the patient's tooth and the cured resin base of each bracket for bonding the brackets to the teeth.

In another and/or alternative embodiment, a bracket to be fitted into the at least one cavity of the transfer tray is provided with a cured resin base or covered with an adhesive. Examples of such brackets are those sold by 3M under the tradenames APC Flash and APC Flash-free. Such bracket can be used, because the at least one cavity of the transfer tray does not fit the entire bracket, but only the proximal portion of the bracket. Using a specific tool, such brackets can be grapped at their wings such that the base remains untouched upon fitting the bracket into the cavity of the transfer tray.

In yet another and/or alternative embodiment, a bracket to be fitted into the at least one cavity of the transfer tray, the bracket is provided with an adhesive on its base. Using such brackets render bonding the brackets to the tooth by introducing a curable resin between the tooth and the bracket as positioned by means of the transfer tray unnecessary.

This procedure is of particular advantage when brackets comprising unique individual bases are to be used, because the unique individual base of each bracket is formed while the transfer tray is present on the plaster model of the patient's teeth. Hence, it is not that crucial to use the appropriate amount of curable resin for forming the unique individual bases, because excess resin can be removed easily without bothering the patient. Since the curable resin does not bind to the plaster of the positive tooth model after being cured, the transfer tray can be removed from the positive tooth model still bearing the brackets, wherein each of the brackets is provided with its unique individual base. The assembly is transferred into the patient's mouth, and only a very little amount of liquid adhesive/resin is required for bonding the brackets to the teeth.

The cavities within the transfer tray securely hold each bracket, even though only the distal part of each bracket is accommodated in form-fitting manner; and it is much easier to remove the transfer tray from the patient's mouth after the brackets have been attached to the teeth. It is less likely that removal of the tray breaks off a bracket. In addition, the method of the present invention facilitates manufacturing to and positioning of individualized brackets, because the resin for attaching the bracket to the tooth likewise provides the individualized base for the bracket.

What is claimed is:

1. A positive tooth model, comprising: a model tooth; a model gum attached to the model tooth; a partial mock bracket attached to the model tooth; and a place holder, wherein
    the partial mock bracket comprises a fully formed distal tie wing and no proximal tie wing;
    the place holder replaces the proximal tie wing of the partial mock bracket and extends in a form of a rod or protrusion in a perpendicular direction starting from a horizontal median of the partial mock bracket to the gum of the tooth model.

2. The positive tooth model according to claim 1, wherein the positive tooth model comprises at least two mock brackets and a place holder for each mock bracket.

3. The positive tooth model according to claim 1, wherein the model tooth and the model gum are manufactured by rapid prototyping to form a progenitor tooth model.

4. The positive tooth model according to claim 1, wherein the positive tooth model comprises at least one line and/or at least one area of a different color than the body of the positive tooth model, said at least one line and/or at least one area indicating a position for positioning the mock bracket and/or indicating a line along which a transfer tray should be excised.

5. The positive toot model according to claim 1, wherein the model tooth comprises an elevated area, said elevated area representing a position for adhering a real bracket on a tooth of a patient and/or representing a unique individual base of the bracket for the tooth of the patient.

6. A positive tooth model, comprising: a model tooth; a model gum attached to the model tooth; a real bracket; and a place holder, wherein the place holder extends perpendicular starting from a horizontal median of the real bracket down to the model gum, and wherein a distal portion of the place holder is formed as a negative model of a proximal tie wing of the real bracket, and the proximal tie wing of the real bracket is engaged into the distal portion of the place holder in a form-fitting manner.

* * * * *